(12) United States Patent
Porter (10) Patent No.: US 9,095,302 B2
(45) Date of Patent: Aug. 4, 2015

(54) METHOD TO GENERATE MAGNETIC RESONANCE EXPOSURES

(75) Inventor: David Andrew Porter, Poxdorf (DE)

(73) Assignee: Siemens Aktiengesellschaft, Munich (DE)

(*) Notice: Subject to any disclaimer, the term of this patent is extended or adjusted under 35 U.S.C. 154(b) by 508 days.

(21) Appl. No.: 13/554,268

(22) Filed: Jul. 20, 2012

(65) Prior Publication Data

US 2013/0033262 A1   Feb. 7, 2013

(30) Foreign Application Priority Data

Aug. 2, 2011  (DE) .......................... 10 2011 080 254

(51) Int. Cl.
| | | |
|---|---|---|
| *A61B 5/00* | (2006.01) | |
| *A61B 5/055* | (2006.01) | |
| *G01R 33/563* | (2006.01) | |
| *G01R 33/567* | (2006.01) | |
| *G01R 33/56* | (2006.01) | |
| *G01R 33/561* | (2006.01) | |

(52) U.S. Cl.
CPC ............... *A61B 5/4064* (2013.01); *A61B 5/055* (2013.01); *G01R 33/5676* (2013.01); *G01R 33/56341* (2013.01); *G01R 33/5602* (2013.01); *G01R 33/5616* (2013.01)

(58) Field of Classification Search
CPC ........... G01R 33/5602; G01R 33/5616; G01R 33/5676; G01R 33/56341; A61B 5/055; A61B 5/4064

See application file for complete search history.

(56) References Cited

U.S. PATENT DOCUMENTS

| | | | |
|---|---|---|---|
| 7,205,763 B2 | 4/2007 | Porter | |
| 7,417,427 B2* | 8/2008 | Porter | 324/306 |
| 8,461,840 B2* | 6/2013 | Stemmer | 324/309 |
| 8,570,034 B2* | 10/2013 | Stemmer | 324/309 |
| 8,947,085 B2* | 2/2015 | Feiweier | 324/309 |
| 2005/0237057 A1 | 10/2005 | Porter | |

OTHER PUBLICATIONS

Andreisek et al.: "Synthetic-Echo Time Postprocessing Technique for Generating Images with Variable T2-weighted Contrast: Diagnosis of Meniscal and Cartilage Abnormalities of the Knee" in Radiology 254, 210, S. 188-199, 2010.
Ong, et al.: "A new approach for simultaneous measurement of ADC and T2 from echoes generated via multiple coherence transfer pathways", Journal of Magnetic Resonance 173, 2005, S. 153-159.
Schellinger et al.: "A Standardized MRI Stroke Protocol Comparison with CT in Hyperacute Intracerebral Hemorrhage", Stroke, 1999, pp. 765-768.

* cited by examiner

*Primary Examiner* — Dixomara Vargas
(74) *Attorney, Agent, or Firm* — Schiff Hardin LLP (57) ABSTRACT

In a method described for generating magnetic resonance exposures in which diffusion-coded raw data are acquired with of a diffusion gradient measurement sequence having a number of partial diffusion gradient sequences, at least one diffusion coding gradient pulse is emitted in each partial data set, and raw data of a k-space region are acquired during a first echo after a defined first echo time the k-space regions in total covering a complete k-space. Raw data of an established navigator k-space region are acquired during a second echo after a second echo time the navigator k-space region being identical for different partial diffusion gradient sequences. Reference raw data are acquired by a reference measurement sequence with multiple partial reference sequences.

13 Claims, 6 Drawing Sheets

METHOD TO GENERATE MAGNETIC RESONANCE EXPOSURES

BACKGROUND OF THE INVENTION

1. Field of the Invention

The present invention concerns a method to generate magnetic resonance exposures of an examination subject, in particular diffusion-weighted magnetic resonance exposures. "Magnetic resonance exposures" in this context means image data representing the interior of the examination subject generated with a magnetic resonance apparatus controlled in accordance with such a method, as well as parameter maps that reflect a spatial or temporal distribution of specific parameter values within the examination subject and that can be generated from the image data, for example. Moreover, the present invention concerns a control device for a magnetic resonance system as well as a magnetic resonance system with which such a method can be implemented.

2. Description of the Prior Art

Diffusion-weighted magnetic resonance exposures are magnetic resonance exposures with which the diffusion movement of specific substances (in particular water molecules) can be measured (detected) in the tissue of the body and can be shown with spatial resolution. Diffusion imaging has become established in the clinical routine, particularly for stroke diagnosis, since the stroke-susceptible brain regions are already apparent markedly earlier in diffusion-weighted images than in classical magnetic resonance exposures. Diffusion tensor imaging, in which the directional dependency of the diffusion is also detected, is a variant of diffusion-weighted magnetic resonance tomography. Diffusion-weighted magnetic resonance exposures herein encompass both magnetic resonance exposures generated within the scope of diffusion-weighted magnetic resonance tomography and magnetic resonance exposures generated within the scope of diffusion tensor imaging.

Diffusion-coded raw data must initially be acquired for the generation of diffusion-weighted magnetic resonance exposures. This takes place with special measurement (data acquisition) sequences that are designated as diffusion gradient measurement sequences in the following. In these measurement sequences, it is characteristic that, after a typical flipping of the relevant nuclear spins in one plane perpendicular to the basic magnetic field of the magnetic resonance scanner, a gradient magnetic field that varies the field strength of the external magnetic field in a predetermined direction is switched (activated) for a predetermined pulse length. The precessing nuclei thereby go out of phase, which is noticeable in the measurement signal.

Presently, diffusion-weighted exposures are typically made by a technique known as a "single shot" method. Within the pulse sequence, an excitation for the entire image (i.e. the complete spatial coding of an image) takes place after a single excitation pulse. One advantage of this method is that the phase effects used within the scope of the diffusion-weighted magnetic resonance tomography do not generate any additional movement artifacts.

An alternative is the use of measurement sequences in which multiple supplementary partial segments of k-space are acquired in succession in a "multi-shot" method, with the partial segments subsequently being combined. Methods known as "readout-segmented echo planar imaging" methods (rs-EPI methods) are among such measurement sequences. These methods have the advantage that information can be drawn from multiple exposures, and specific artifacts thus can be reduced. In addition, the image quality can be improved. In diffusion-weighted acquisition methods, however, it is precisely movements of specific substances that should be detected by utilizing the phase effects. If a data acquisition takes place with a multi-shot method and movements of the patient or of the organs occurs between the individual pulse sequences, this can lead to severe movement artifacts. Therefore, in such diffusion-weighted multi-shot methods, what is known as a navigator correction is implemented in which, each time raw data are acquired in a partial segment of k-space within the scope of a first echo, raw data are acquired from a middle k-space region in a subsequent second echo (known as the "navigator echo"), and thus a complete image with relatively low resolution is created. This resolution of the navigator image is good enough that the phase variations are perceptible in this image, and thus the images acquired in the navigator echo can be used in order to implement a correction of the individual shots based on one another.

In diffusion imaging, multiple images with different diffusion directions and weightings (i.e. with different diffusion coding gradient pulses) are normally acquired and combined with one another. The strength of the diffusion weighting is defined by what is known as the "b-value". The different diffusion images, or the images or parameter maps combined from these diffusion images, can then be used for the desired diagnostic purposes. In order to be able to correctly estimate the influence of the diffusion movement, an additional reference exposure is normally necessary in which no diffusion coding gradient pulse is activated, i.e. an image with b=0. The pulse measurement sequence to acquire the reference data is designed in the same manner as the diffusion gradient measurement sequence, with the exception of the omission of the diffusion coding gradient pulses.

In addition to the diffusion-weighted images, $T_2$-weighted exposures are still additionally generated in the typical clinical application since these show an important contrast for specific pathology information, in particular given tumors and strokes. $T_2^*$-weighted exposures are likewise frequently additionally produced since these have a higher sensitivity with regard to hemorrhages. Therefore, such $T_2^*$-weighted exposures are advantageous particularly in the case of a stroke in which the diffusion-weighted exposures are also of particular value.

It has previously been disadvantageous in the case of multi-shot diffusion-coded acquisitions that neither the pulse sequences for the diffusion-weighted images nor the pulse sequences for the reference images required to evaluate the diffusion-coded can additionally be used to generate $T_2$-weighted or $T_2^*$-weighted images. This is due to the fact that an optimally short echo time is desirable for the diffusion-weighted acquisitions in order to reduce the signal losses due to the $T_2$ decay, and thus to maximize the signal-to-noise ratio. In single-shot diffusion-coded acquisitions, the image quality is too poor in order to use them as $T_2$- or $T_2^*$-weighted images. An additional advantage of an optimally short echo time is that a short repetition time is then possible. Longer echo times, however, are required for $T_2$-weighted acquisitions and $T_2^*$-weighted acquisitions since then it is precisely the (long) $T_2$ decay that includes the significant information.

SUMMARY OF THE INVENTION

An object of the present invention is to provide a method to generate diffusion-weighted magnetic resonance exposures and a control device suitable for operating a magnetic resonance system for that purpose, in which method and control device a reduction of the total measurement times is enabled in examinations that include diffusion-weighted magnetic resonance acquisitions.

Within the scope of the method according to the invention, this object is achieved by controlling the magnetic resonance apparatus to generate the magnetic resonance exposures as follows.

Diffusion-coded raw data are acquired by executing a diffusion gradient measurement sequence. This diffusion gradient measurement sequence includes a number of partial diffusion gradient sequences, with at least one diffusion coding gradient pulse—normally multiple diffusion coding gradient pulses—being emitted in each partial diffusion gradient sequence in addition to the typical excitation pulses, refocusing pulses and gradient pulses for spatial coding. Moreover, after a defined first echo time, raw data of a k-space region (k-space segment) are acquired during a first echo during each partial diffusion gradient sequence, meaning that a corresponding echo signal is detected by means of suitable reception antennas. The partial diffusion gradient sequences are respectively designed so that the k-space regions in which raw data are acquired during different partial diffusion gradient sequences cover at least one predetermined k-space in total. In other words, in a multi-shot method, k-space is scanned in segments in order to thus improve the SNR and the image quality in the diffusion-weighted magnetic resonance exposures.

Raw data of a navigator k-space region that is established in common for all partial diffusion gradient sequences—i.e. is identical for different partial diffusion gradient sequences—are additionally acquired during each partial diffusion gradient sequence. This takes place after receiving the first echo, during a second echo (also called a "navigator echo" in the following) after a defined second echo time.

It should be noted that the k-space regions from which raw data are acquired in a second echo during different partial diffusion gradient sequences do not need to be completely identical. It is only important that, within the particular k-space region, there is at least one common, identical k-space region that can form the navigator k-space region. This latter region preferably is the central k-space region, such that a complete image of the respective slice is generated every time by the acquisition of the raw data, which complete image has a sufficient resolution in order to correct movement artifacts that arise due to k-space being scanned in segments during the first echo.

Also within the scope of the method, raw reference data are acquired by means of a reference measurement sequence. This can take place before or after acquisition of the raw diffusion-coded data. This reference measurement sequence also has a number of partial reference sequences, wherein each partial reference sequence in turn has (in the typical manner) excitation and refocusing radio-frequency pulses as well as gradient pulses for spatial coding. Different than the partial diffusion gradient sequence, however, this partial reference sequence has no diffusion-coding gradient pulses, or possibly only diffusion-coding gradient pulses with very low gradient field strength, such that they can be used as reference images with b≈0. During each partial reference sequence, first raw reference data of a k-space region are acquired again during a first echo after the defined first echo time, wherein again the k-space regions from which raw data are acquired during different partial reference sequences in total cover at least the predetermined k-space. In contrast to the partial diffusion gradient sequence, however, in the partial reference sequence as well second reference raw data of a k-space region are respectively acquired during a second echo after a second echo time, wherein the k-space regions here also in total likewise cover at least the predetermined k-space.

Given the acquisition of the reference raw data in the second echo, its use as a navigator echo is now to be omitted, which is different than in the known rs-EPI method to generate diffusion-weighted magnetic resonance exposures. Since the reference raw data are acquired without a diffusion coding, in these measurements there is no need to fear that movement artifacts occur due to phase effects. Therefore, the navigator echo is not required in the reference measurement. The additional raw data—instead of the acquired raw data—of complete k-space allow a reconstruction of additional, higher resolution reference image data at a second echo time, which additional reference image data can be used (depending on a more precise embodiment of the reference measurement sequence) to generate different additional magnetic resonance exposures. This in turn allows a portion of the otherwise additionally implemented measurements (for example to generate $T_2$- or $T_2^*$-weighted image data) to be omitted, so that overall the measurement time in such an examination can be reduced with the method according to the invention.

Both the diffusion gradient measurement sequence and the reference measurement sequence are typically implemented repeatedly in succession in order to measure a specific volume in slices. In principle, however, it is also possible for a measurement not to be slice-selective, but rather data for a larger volume are acquired.

A control device according to the invention for a magnetic resonance system requires (among other things), the following components.

A radio-frequency (RF) transmission device is required to transmit radio-frequency pulses to a transmission antenna system of the magnetic resonance system. For example, this transmission antenna system can be a typical body coil arranged around a measurement space for the patient in the tomograph, or can also be a local coil system. The radio-frequency transmission device has a number of components, among other things low-power signal generators which ensure that the matching radio-frequency pulses are initially generated with low amplitude, and suitable radio-frequency power amplifiers in order to feed the radio-frequency pulses into the antennas with the required power. Furthermore, monitoring components are provided to ensure that the radio-frequency power is within the limit values predetermined by the SAR standards (SAR=Specific Absorption Rate), etc.

Furthermore, the control device requires a gradient system interface to control a gradient system of the magnetic resonance system, i.e. a suitable interface with which the gradient pulses are generated and then fed into the different gradient coils of the gradient system.

In addition to this, a radio-frequency reception device is required to acquire raw data via a reception antenna system of the magnetic resonance system. This reception antenna system can be the same system as the transmission antenna system if this can be switched accordingly between a transmission mode and a reception mode. These are normally suitable local coils. The radio-frequency reception device accordingly has a number of acquisition channels in which the signals captured by the individual antennas of the reception antenna system (and additionally preprocessed as necessary, under the circumstances also converted into modes) are accepted and processed further, in particular are amplified and digitized.

Finally, the control device requires a sequence control unit that, to generate magnetic resonance exposures of an examination subject, during operation transmits sequence control data to the radio-frequency transmission device, the gradient system interface and the radio-frequency reception device so that at least the diffusion gradient measurement sequence that is described above for acquisition of diffusion-coded raw data and the reference measurement sequence to acquire reference raw data are emitted.

In addition to a basic field magnet system with which a basic magnetic field is typically applied in the patient measurement space, a magnetic resonance system according to the invention must have a transmission antenna system (described above), a gradient system comprising multiple gradient coils, a reception antenna system, and a control device according to the invention (described in the preceding).

The sequence control unit preferably is realized in the form of software in a suitably programmable control device with appropriate storage capabilities. The radio-frequency transmission device, the gradient system interface and the radio-frequency reception device can also be realized at least partially in the form of software units, wherein other units of these components are purely hardware units, for example the radio-frequency amplifier, the radio-frequency transmission device, a gradient pulse generator device of the gradient system interface or an analog/digital converter of the radio-frequency reception device, etc. A realization largely in software—in particular of the sequence control unit—has the advantage that even magnetic resonance system control devices that have already been in use can be upgraded in a simple manner via a software update in order to operate in the manner according to the invention. Therefore, the above object is also achieved by a non-transitory computer-readable data storage medium that is stored in a portable memory and/or is provided for transmission via a network and thus can be loaded directly into a memory of a programmable magnetic resonance system control device. The data storage medium embodies programming instructions (commands) that cause all steps of the method according to the invention to be implemented when said program is executed in the control device.

In a preferred development of the method, the reference measurement sequence is designed so that image data can respectively be reconstructed with an identical spatial resolution on the basis of the first reference raw data and the second reference raw data. This simplifies a later combination of the image data into joint (common) image data.

There are various possibilities for the precise design of the reference measurement sequences or, respectively, of the partial reference sequences. In a preferred variant, within the partial reference sequence a refocusing pulse is respectively emitted after the first echo and before the second echo. This leads to the situation that the second echo is also what is known as a "spin echo", and that the raw data acquired during this spin echo can be used in order to generate $T_2$-weighted image data. In an alternative preferred method, such a second refocusing pulse is omitted. Instead of this, the second echo (which in this case is a gradient echo) is merely generated via the switching of a readout gradient after the desired second echo time. $T_2^*$-weighted image data can be generated from the raw data that are thereby acquired.

Which of these two variants is selected depends on which additional images should more preferably be produced within the complete examination.

Within the scope of the method according to the invention, multiple diffusion gradient measurement sequences are advantageously implemented with different diffusion gradient strengths to acquire different diffusion-coded raw data. Image data of the examination subject that are diffusion-weighted to different degrees are then generated on the basis of the different diffusion-coded raw data. Independent of how many different diffusion gradient measurement sequences are implemented, the generation of the diffusion-weighted image data normally takes place via reconstruction from the raw data of the first echo, wherein the raw data of the second echo are respectively used to correct the movement artifacts. Finally, parameter maps with particular diagnostic significance are generated via a combination of the image data that are diffusion-weighted to different degrees, which parameter maps reflect the "Apparent Diffusion Coefficient (ADC)" or the "Fractional Anisotropy (FA)".

In this method—normally independently of how many different diffusion gradient measurement sequences are implemented with different diffusion gradient strengths—only one b=0 measurement (i.e. only one reference measurement) is required that is then used in the determination of the parameter maps for the evaluation of the diffusion-weighted data that is described above. In some examinations, however, multiple b=0 measurements can also be made, for example in order to improve the SNR or in order to monitor movements in longer scans. Insofar as the reference raw data are acquired with only a small diffusion gradient instead of with b=0, suitable parameter maps can possibly also already be generated on the basis of these raw data in combination with the more strongly diffusion-weighted raw data, without even more diffusion-coded raw data being generated with other diffusion gradient strengths.

As explained above, the special reference measurement sequence within the method according to the invention allows a generation of additional image data based on the raw data measured in the first echo and in the second echo during the reference measurement sequence.

Synthetic image data with a defined effective echo time that lies outside of the first echo time and the second echo time are advantageously generated on the basis of the first reference raw data and the second reference raw data. "Outside" in this sense means that the effective echo time lies between the first echo time and the second echo time, below the shorter echo time or above the longer echo time. This effective echo time particularly preferably lies between the first echo time and the second echo time. Depending on the precise design of the reference measurement sequence—i.e. dependent on whether the second echo is a spin echo or a gradient echo— the synthetic image data are $T_2$-weighted or $T_2^*$-weighted image data. In other words, synthetic $T_2$-weighted or $T_2^*$-weighted image data are generated via a suitable combination for example, which synthetic image data correspond to those "real" image data that would be reconstructable on the basis of raw data acquired with an effective echo time that lies outside of advantageously between) the first echo time and the second echo time.

As explained, it has previously been the case that $T_2$-weighted and/or $T_2^*$-weighted image data are always additionally generated that typically must have a longer echo time than the first defined echo time that is used within the scope of the diffusion-weighted measurements. Via the possibility of the generation of synthetic $T_2$-weighted or synthetic $T_2^*$-weighted image data with an arbitrary echo time between the first echo time and second echo time, an additional measurement to generate such $T_2$-weighted or $T_2^*$-weighted measurements can now be foregone. Without any additional measures, the time savings that is thereby achieved outweighs the additional time that—in contrast to a previously typical single shot method—is required to implement the multi-shot method for the diffusion-weighted measurements. Overall, significantly qualitatively better diffusion-weighted image data can thus be generated with the method according to the invention than with the previous methods in approximately the same or even shorter total measurement times.

In principle, it is possible for synthetic raw data to be generated directly by a combination of the reference raw data of the first echo and of the second echo, and that the desired synthetic image data are then reconstructed on this basis.

One possibility to combine the raw data acquired in two successive echo times to form synthetic image data is, for example, to initially calculate maps of the $T_2$ relaxation times and the proton density that vary on a logarithmic scale, and then to generate the new image data based on these parameters. This means that a local function for the $T_2$ decay is respectively determined for each image point, and then an average $T_2$ value can be calculated from this after an arbitrary echo time. For example, such a method is described in the article by Andrelsek G, White L M, Theodoropoulus J S, Naraghl A, Yhao C Z, Mamisch T C, Sussman M S, "Synthetic-echo time postprocessing technique for generating images with variable T2-weighted contrast: diagnosis of meniscal and cartilage abnormalities of the knee" in Radiology, 2010; 254(1): 188-199.

However, first image data are advantageously initially generated on the basis of the first reference raw data and second image data are generated on the basis of the second reference raw data, wherein (as was previously described) these second image data advantageously have the same spatial resolution as the first image data. The synthetic image data are subsequently generated via a geometric averaging of the first image data and the second image data. In contrast to the previously cited method, this has the advantage that a logarithmic scale does not hereby need to be used. Namely, if the noise at an image point is higher at the second echo (at which the second $T_2$ value is determined for the determination of the local T2 decay function) than at the first echo (at which the first $T_2$ value is determined), the second $T_2$ value can be higher than the first $T_2$ value. In the aforementioned method, at this image point this can lead to an invalid effective $T_2$ value. An additional problem occurs when the two signal values of the first echo and second echo lead to a difference close to zero. A infinitely high $T_2$ value then occurs that causes numerical problems in the evaluation.

Such a method to generate magnetic resonance exposures of an examination subject—in which first raw data that are acquired after a first echo time within a measurement sequence with a number of partial sequences and in which second raw data are acquired after a second echo time within a measurement sequence with a number of partial sequences—is always reasonable in order to generate synthetic image data with a defined echo time that lies outside of (advantageously between) the first echo time and the second echo time. This means that, independent of whether the raw data are the first reference raw data and the second reference raw data in the method according to the invention, first image data can always be initially generated on the basis of the first raw data, and second image data can always be initially generated on the basis of the second raw data, and after this the synthetic image data are then generated on the basis of the first image data and the second image data. This magnetic resonance exposure generation method can inasmuch also be viewed as an independent advantageous idea. This method thus offers an advantage in, for example, nearly all double echo, spin echo and gradient echo sequences.

In order to realize this advantageous combination method, an image data processing unit is required to generate magnetic resonance exposures of an examination subject, which image data processing unit has an image data interface to accept first image data that were reconstructed on the basis of first raw data acquired after a first echo time, and to accept at least second image data that were reconstructed on the basis of second raw data acquired after a second echo time. The image data processing unit additionally requires an image data combination unit in order to generate, via a geometric averaging of the first image data and at least the second image data, synthetic image data with a defined echo time that lies outside of (advantageously between) the first echo time and the second echo time. The image data processing unit can additionally also have an interface to output the synthetic image data.

The image data processing unit can also be part of a magnetic resonance system, for example be integrated into a control device of the magnetic resonance system. Inasmuch a realization in the form of suitable software is also possible here and is advantageous for easier retrofitting of existing control devices. In this case the interfaces can also be designed as software in order to accept image data already present in other software modules or, respectively, to output image data to these. The interfaces to accept the first and second image data can also be two separate sub-interfaces that respectively accept the first or second image data. The output interface can likewise be combined with the interfaces to accept the image data. In particular, the image data processing unit can also be integrated directly into a reconstruction unit that serves to reconstruct the image data from the raw data. Alternatively, the image data processing unit can be realized as a separate device and/or at a workstation designed for this, which device and/or workstation can accept image data and output them again via a network or the like.

The method described above is not limited to the combination of two image data sets from different echo times, but rather image data from multiple echoes can also be combined in a similar manner. In particular, it is possible to supplement the preferred image data combination methods (described in detail in the following) with more than two image data sets in an analogous manner.

The generation of the synthetic image data preferably takes place using a geometric averaging of the first image data and the second image data, which averaging is weighted using a predetermined weighting factor. The "virtual" echo time of the synthetic image data can be arbitrarily set between the first echo time and the second echo time via this weighting factor. A generation of synthetic image data with a virtual echo time below the first echo time and above the second echo time is analogously possible via an interpolation. However, a virtual echo time between the first echo time and second echo time is always assumed as an example for the further explanations.

This procedure of a weighted geometric averaging of the image data can theoretically be explained as follows. For this it can be assumed that the signal in each voxel can be represented by an individual exponential model, such that the signals $S_1$ and $S_2$ measured during the two echoes can respectively be expressed by the following equations:

$$S_1 = A \cdot \exp\left(-\frac{TE_1}{T_2}\right) \tag{1a}$$

$$S_2 = A \cdot \exp\left(-\frac{TE_2}{T_2}\right) \tag{1b}$$

$TE_1$ and $TE_2$ are the echo times for the first and second echo, and $T_2$ is the transversal relaxation time.

The signal $S_s$ at an image point (pixel or, respectively, voxel) of a synthetic image with a specific predetermined echo time $TE_s$ can then be generated via a weighted geometric averaging of these two signals $S_1$ and $S_2$, as follows:

$$S_S = \sqrt[w+1]{(S_1)^w S_2} \tag{2}$$

The value of the weighting factor w used in this simple equation depends on the desired echo time $TE_s$ for the generated synthetic image. The relationship between these parameters can be obtained in that Equation (2) is rewritten in the following form:

$$A \cdot \exp\left(-\frac{TE_S}{T_2}\right) = \left(\left(A \cdot \exp\left(-\frac{TE_1}{T_2}\right)\right)^w \cdot A \cdot \exp\left(-\frac{TE_2}{T_2}\right)\right)^{\frac{1}{w+1}} \tag{3}$$

This equation can be simplified as follows:

$$A \cdot \exp\left(-\frac{TE_S}{T_2}\right) = A \cdot \exp\left(-\frac{w \cdot TE_1 + TE_2}{(w+1)T_2}\right) \tag{4}$$

Equation (4) is satisfied precisely when the following condition applies:

$$w = \frac{TE_2 - TE_S}{TE_S - TE_1} \tag{5}$$

Given a known first echo time $TE_1$ and a known second echo time $TE_2$, a matching weighting factor w can thus be calculated with the aid of Equation (5) for an arbitrary effective echo time $TE_s$ lying between the first echo time $TE_1$ and the second echo time $TE_2$. This can then be used in order to implement a combination of the signals $S_1$, $S_2$ for the individual image points of the image data reconstructed from the raw data of the first and second echoes according to Equation 2, and thus to obtain the synthetic image with the desired echo time.

Equation (5), moreover, shows that—when a weighting factor w=1 is selected—as expected the result of the (therefore unweighted) geometric averaging of the data of the two echo times leads to a synthetic image with an effective echo time corresponding to the arithmetic mean of the two echo times $TE_1$ and $TE_2$.

The described generation of the synthetic image data on the basis of an averaging (weighted per image point, i.e. per voxel or pixel) of the image data respectively reconstructed on the basis of the raw data generated during the first echo and during the second echo is a particularly effective and fast method.

DESCRIPTION OF THE PREFERRED EMBODIMENTS

Figure 1:
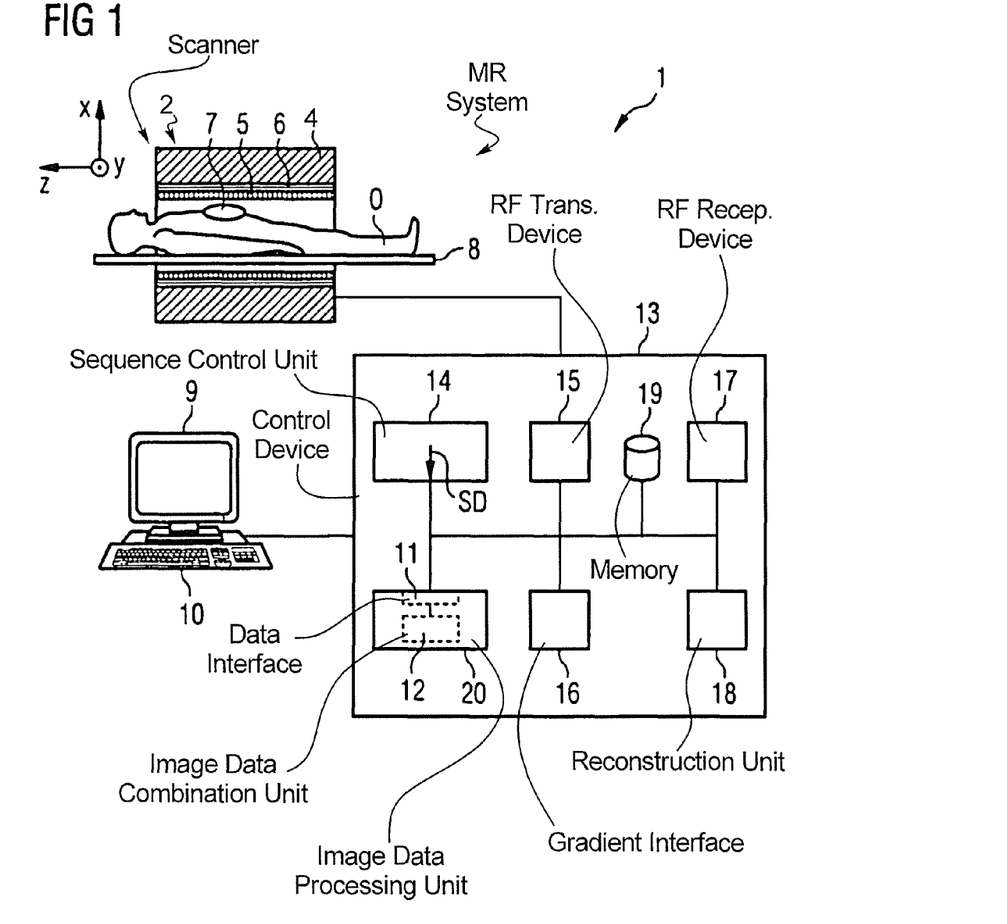
FIG. 1 schematically illustrates a magnetic resonance system according to an exemplary embodiment of the invention.

A magnetic resonance system 1 (abbreviated as an "MR system" in the following) according to the invention is shown in a roughly schematic manner in FIG. 1. The system 1 includes the actual magnetic resonance scanner 2 with an examination space 3 or patient tunnel into which an examination subject O (here a patient or test subject in whose body the examination subject—a defined organ, for example—is located) on a bed 8 can be introduced.

The magnetic resonance scanner 2 is typically equipped with a basic field magnet system 4, a gradient system 6, and an RF transmission antenna system 5 and an RF reception antenna system 7. In the shown exemplary embodiment, the RF transmission antenna system 5 is a whole-body coil permanently installed in the magnetic resonance scanner 2, in contrast to which the RF reception antenna system 7 includes local coils to be arranged on the patient or test subjects (symbolized only by a single local coil in FIG. 1). However, in principle the whole-body coil can also be used as an RF reception antenna system and the local coils can also be used as an RF transmission antenna system, insofar as these coils can respectively be switched into different operating modes.

The MR system 1 furthermore has a central control device 13 that is used to control the MR system 1. This central control device 13 includes a sequence control unit 14 for pulse sequence control. In this the sequence of radio-frequency pulses (RF pulses) and gradient pulses is controlled depending on a selected imaging sequence. Such an imaging sequence can, for example, be predetermined within a measurement or control protocol. Different control protocols for different measurements are typically stored in a memory 19 and can be selected by an operator (and possibly modified as necessary) and then be used to implement the measurement.

To output the individual RF pulses, the central control device 13 has a radio-frequency (RF) transmission device 15 that generates and amplifies the RF pulses and feeds them into the RF transmission antenna system 5 via a suitable interface (not shown in detail). The control device 13 has a gradient interface 16 to control the gradient coils of the gradient system 6. The sequence control unit 14 communicates in a suitable manner (for example by transmitting sequence control data SD) with the radio-frequency transmission device 15 and the gradient system interface 16 to emit the pulse sequences. The control device 13, moreover, has a radio-frequency reception device 17 (likewise communicating with the sequence control unit 14 in a suitable manner) in order to acquire magnetic resonance signals (i.e. raw data) that are received as coordinated by the RF transmission antenna system 7. A reconstruction unit 18 accepts the acquired raw data and reconstructs the MR image data from these. These image data can then be stored in the memory 19, for example, and/or be processed further in an image data processing unit 20 in order to generate other image data and/or parameter maps (from different image data, for example) that can in turn likewise be stored in the memory 19. This image data processing unit 20 has an image data interface 11 to accept first image data that were reconstructed by the reconstruction unit 19 on the basis of first raw data acquired after a first echo time, and to accept second image data that were reconstructed on the basis of second raw data acquired after a second echo time. As is explained again later using FIG. 2, synthetic image data with a defined effective echo time that lies between the first echo time and the second echo time are then generated in an image data combination unit 12 on the basis of the first image data and the second image data.

These synthetic image data can be output again via the image data interface 11, for example can be stored in the memory 19. Alternatively, the image data processing unit 20—in particular the image data combination unit 12—here can also be integrated into the reconstruction unit 18 or be connected to the central control device 13 externally via a network or the like.

An operation of the central control device 13 can take place via a terminal with an input unit 10 and a display unit 9 via which the entire MR system 1 can thus also be operated by an operator. MR images can also be displayed at the display unit 9 and measurements can be planned and started by means of the input unit 10 (possibly in combination with the display unit 9), and in particular suitable control protocols can be selected (and possibly modified) with suitable measurement sequences.

The MR system 1 according to the invention, and in particular the control device 13, can have a number of additional components (not shown in detail here but typically present in such apparatuses), for example a network interface in order to connect the entire system with a network and be able to exchange raw data and/or image data, or parameter maps, as well as additional data, for example patient-relevant data or control protocols.

The acquisition of raw data can be acquired by radiation of RF pulses and the generation of gradient fields, and the reconstruction of MR images therefrom, are fundamentally known to those skilled in the art and thus need not be explained in detail herein. The most varied measurement sequences—for example EPI measurement sequences or measurement sequences to generate diffusion-weighted images—are similarly known in principle to those skilled in the art.

Figure 2:
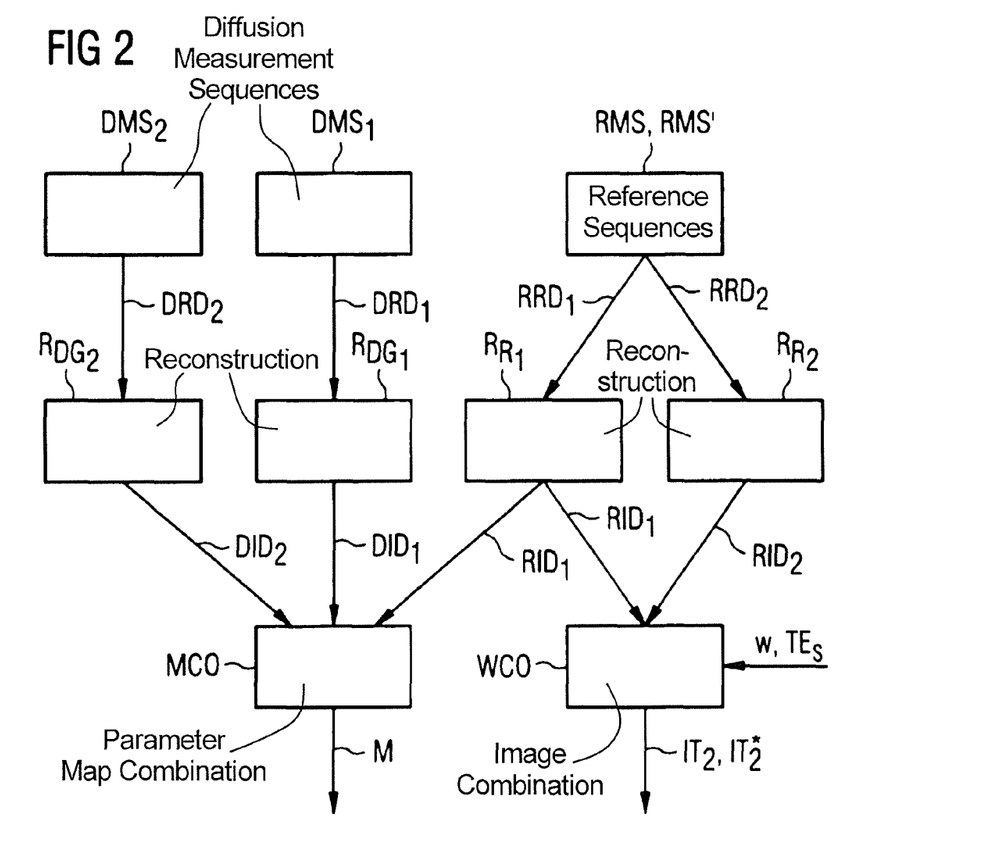
FIG. 2 is a flow chart showing the basic steps to generate magnetic resonance exposures according to an exemplary embodiment of the invention.

FIG. 2 shows a flow chart for a measurement workflow in which the method according to the invention can be used. In this method, diffusion-coded raw data are respectively initially measured with different diffusion gradient strengths within the scope of multiple diffusion gradient measurement sequences $DMS_1$, $DMS_2$. Each of these diffusion gradient measurement sequences $DMS_1$, $DMS_2$ has a number of measurements for different slices, and for each slice a number of partial diffusion gradient sequences $DMS_i$ are thereby implemented, wherein each partial diffusion gradient sequence $DMS_i$ can (for example) be designed in terms of its shape, as this is shown in the pulse diagram according to FIG. 3.

Figure 3:
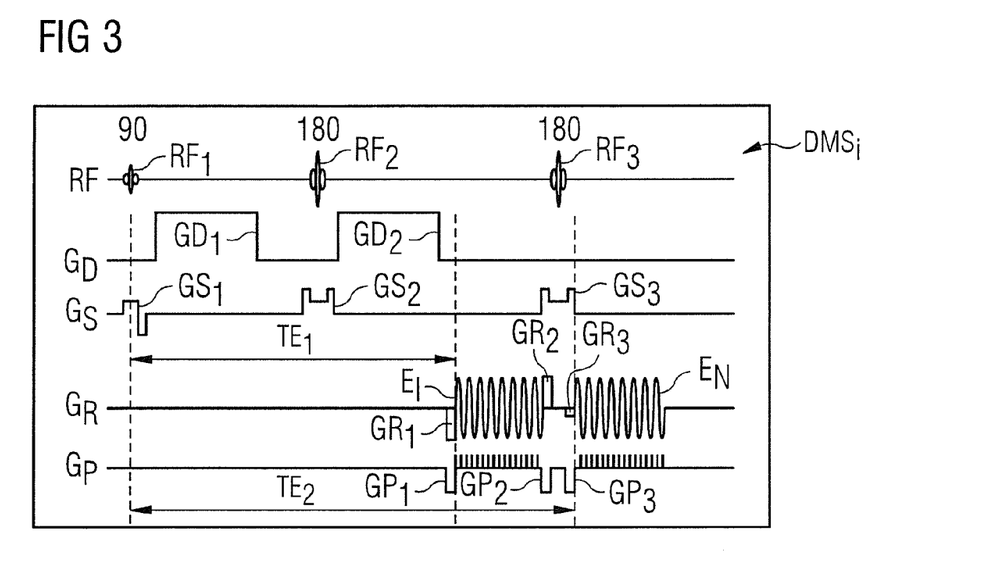
FIG. 3 is a pulse diagram of a partial diffusion gradient sequence for an embodiment of the method according to the invention.

FIG. 3 shows a pulse diagram for a standard diffusion-weighted rs-EPI sequence with a 2D navigator correction. This means that raw data from a different region or, respectively, segment of k-space and additional raw data from a middle k-space region are read out at each partial diffusion gradient sequence $DMS_i$ in order to thus acquire a low-resolution complete image for a later correction of the image data.

FIG. 3 shows the emitted radio-frequency pulses $RF_1$, $RF_2$, $RF_3$ to excite the nuclear spins on the uppermost radio-frequency pulse axis RF.

The diffusion coding pulses $GD_1$, $GD_2$ for diffusion coding are shown on the next lower diffusion gradient axis $G_D$. Via these diffusion coding pulses $GD_1$, $GD_2$ it is ensured that the field strength of the external magnetic field varies in a predetermined direction so that the nuclear magnetization no longer precesses with the same Larmor frequency but rather goes out of phase.

The $GS_1$, $GS_2$, $GS_3$ of the slice selection gradient $G_S$ are shown on the third axis, the gradient pulses $GR_1$, $GR_2$, $GR_3$ of the readout gradient $G_R$ are shown on the fourth axis, and the gradient pulses $GP_1$, $GP_2$, $GP_3$ of the phase coding gradient $G_P$ are shown on the fifth axis.

The pulse sequence initially begins with a first frequency-selective radio-frequency pulse $RF_1$ which is simultaneously emitted with a slice selection gradient pulse $GS_1$ so that the nuclear spins in a specific defined slice are flipped in a typical manner by 90° relative to the basic magnetic field (i.e. in the x/y-plane). A first diffusion coding pulse $GD_1$ is subsequently emitted. The intensity or, respectively, amplitude and duration of this diffusion coding pulse $GD_1$ determines the strength of the diffusion weighting.

A frequency-selective radio-frequency refocusing pulse $RF_2$ is subsequently emitted in parallel with an additional slice selection gradient pulse $GS_2$ in order to achieve a refocusing of the nuclear spins in the selected slice. The orientation of the nuclear magnetization is rotated by 180° via this frequency-selective refocusing pulse $RF_2$. A diffusion coding pulse $GD_2$—which is designed in the same shape as the first diffusion coding pulse $GD_1$—is subsequently switched again. Due to the identical frequency differences in the reverse rotation direction, the magnetic moments of the nuclear spins now partially come into phase again, which leads to the situation that a spin echo can subsequently be measured as an imaging echo $E_I$. The diffusion weighting is generated via the dephasing and rephasing process.

For this a first pre-phase readout gradient pulse $GR_1$ is switched which is changed from one partial diffusion gradient sequence to the next with regard to its amplitude so that different segments or, respectively, regions of k-space are always read out during the first echo $E_1$. A negative phase coding gradient pulse $GP_1$ is set simultaneously with this readout gradient pulse $GR_1$. Multiple very short phase coding gradient pulses subsequently take place during the acquisition of the raw data in order to acquire the image data with phase coding in the desired k-space segment during the entire propagation time of the first echo $E_I$. The emission of the readout gradient pulse $GR_1$ and of the phase coding gradient pulse $GP_1$ takes place exactly at a predetermined first echo time $TE_1$ in relation to the emission of the first excitation pulse $RF_1$.

At the end of the first echo $E_I$, a post-phase gradient pulse $GR_2$ is switched which is likewise changed from partial diffusion gradient sequence $DMS_i$ to partial diffusion gradient sequence $DMS_{i+1}$ with regard to its amplitude. The magnetization is re-phased in the x-direction via this post-phase readout gradient pulse $GR_2$. Overall, a different k-space segment is read out via this pulse series in each partial diffusion gradient sequence, such that k-space later leads [sic] with a subset of $k_x$ respective measurement points via a contiguous set of raw data points for all $k_y$ (i.e. phase-coded) measurement points.

After the first echo $E_I$ has ended, a second 180°, frequency-selective refocusing pulse $RF_3$ is emitted which—due to the simultaneous emission of an additional slice selection gradient pulse $GS_3$—likewise acts only in the desired slice. A pre-phase readout gradient pulse $GR_3$ is then subsequently emitted again, simultaneously with an additional phase coding gradient pulse $GP_3$. In contrast to the first pre-phase readout gradient pulse $GR_1$, this additional pre-phase gradient pulse $GR_3$ is always the same for all partial diffusion gradient pulse DMS; (i.e. with identical amplitude), such that a fixed $k_x$ offset is provided and the same region in k-space (namely the middle k-space region) is always read out in the subsequent second spin echo $E_N$. This second echo $E_N$ is what is known as a 2D navigator echo. A correction of movement artifacts (that could occur since the image data in the first echo $E_I$ were acquired over a longer period of time within the scope of multiple partial diffusion gradient sequences $DMS_i$) can take place in a known manner on the basis of the raw data acquired in this navigator echo EN.

The partial diffusion gradient sequences shown in FIG. 3 are used in both the first diffusion gradient measurement sequence $DMS_i$) and in the second diffusion gradient measurement sequence $DMS_2$ (see FIG. 2), wherein diffusion coding gradient pulses $GD_1$, $GD_2$ of different strengths are used, however. As is shown in FIG. 2, a reconstruction $R_{DG1}$, $R_{DG2}$ is respectively implemented on the basis of the diffusion-coded raw data $DRD_1$, $DRD_2$ acquired during the first echo $E_I$ in order to generate corresponding diffusion-weighted image data $DID_1$, $DID_2$.

Figure 5:
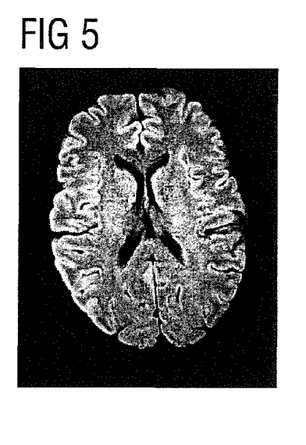
FIG. 5 shows an example of a diffusion-weighted image of a slice through a human head, which image can be generated using partial diffusion gradient sequences according to FIG. 3.

As an example, FIG. 5 shows a diffusion-weighted image with a diffusion weighting of b=1000 s/mm² that was acquired with such a diffusion gradient measurement sequence. For this a magnetic resonance apparatus with a basic magnetic field of 3 Tesla is used. The field of view amounts to 220 mm, the image matrix is 256×256 pixels and the slice thickness is 4 mm.

As was explained above, in addition to these diffusion-weighted images at least one reference measurement must be implemented in which the same slice is acquired without activation of a diffusion gradient. For this a reference measurement sequence RMS, RMS' (see FIG. 2) with a number of partial reference sequences $RMS_i$, $RMS_i'$ can be used, wherein each of the partial reference sequences $RMS_i$, $RMS_i'$ is basically designed just like the partial diffusion gradient sequences $DMS_i$, only with the exception that here no (or at most a very weak) diffusion coding gradient pulse $GD_1$, $GD_2$ is set.

Figure 4:
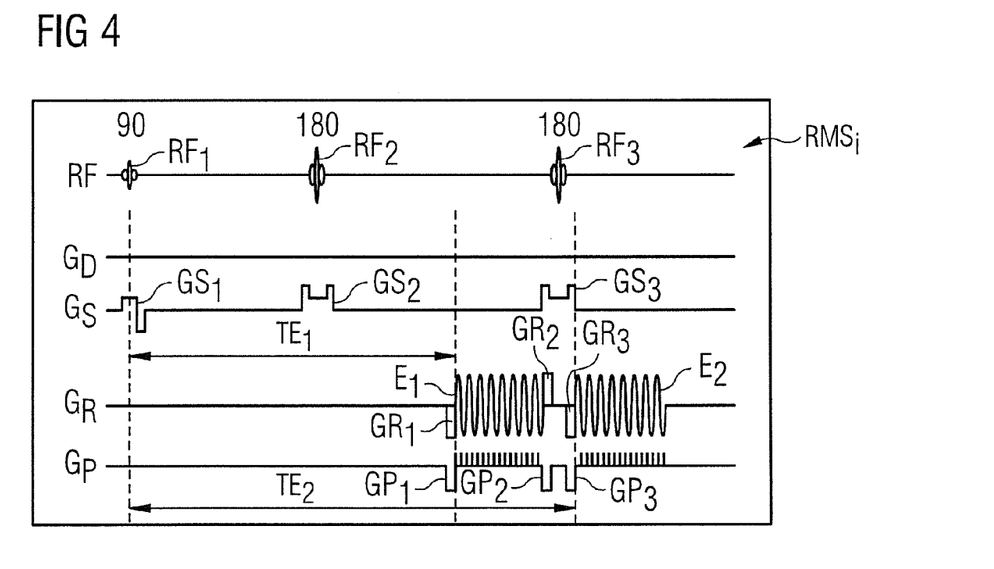
FIG. 4 is a pulse diagram of a partial reference sequence for another embodiment of the method according to the invention.

However, according to the invention the reference measurement sequence RMS with a somewhat modified partial reference sequence $RMS_i$ is now used as they are shown in FIG. 4, for example. As a comparison of FIGS. 4 and 3 shows, the partial reference sequence RMS differs in no way from the partial diffusion gradient sequence DMS; according to FIG. 3, up to and including the emission of the second refocusing pulse $RF_3$. This means that a first echo $E_1$ is read out at precisely the identical first echo time $TE_1$ in the same manner as the first echo $E_1$ in the partial diffusion gradient sequence according to FIG. 3.

However, in contrast to this partial diffusion gradient sequence DMS; according to FIG. 3, an additional pre-phase readout gradient pulse $GR_3$ is now emitted at a second echo time $TE_2$ which can (but does not need to) coincide with the second echo time $TE_N$ in the partial diffusion gradient sequence $DMS_i$, which additional pre-phase readout gradient pulse $GR_3$ is not the same as in the navigator echo $E_N$ for all partial reference sequences $RMS_i$; rather, this pre-phase readout gradient pulse $GR_3$ differs from partial reference sequence $RMS_i$ to partial reference sequence $RMS_{i+1}$ in the amplitude, and in fact in the same manner as the first pre-phase readout gradient pulse $GR_1$ that is switched before readout of the first echo $E_1$. In this way it is ensured that, during the second echo $E_2$ after the second echo time $TE_2$, raw data are acquired again in exactly the same manner (only at a later point in time) as in the first echo $E_1$. In other words, in this reference measurement sequence RMS the same image is acquired twice at the same spatial resolution at different echo times $TE_1$, $TE_2$.

The reference raw data $RRD_1$, $RRD_2$ from the first echo $E_1$ and the second echo $E_2$ that are acquired with multiple such partial reference sequences $RMS_i$ are then supplied to a reconstruction $R_{R1}$ and $R_{R2}$ in order to generate corresponding reference image data $RID_1$, $RID_2$ from these (see FIG. 2).

Figure 6:
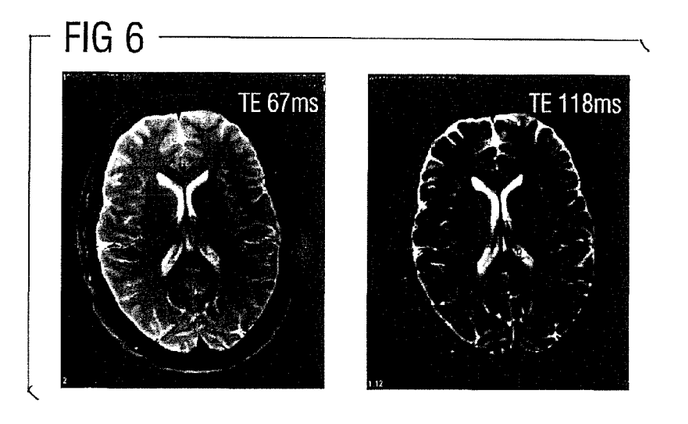
FIG. 6 shows examples of reference images of a slice through a human head corresponding to the diffusion-weighted image from FIG. 5, which reference images can be measured using partial reference sequences according to FIG. 4 at different echo times.

FIG. 6 shows two example images as they can be acquired with the aid of multiple such partial reference sequences $RMS_i$ (as they are shown in FIG. 4). The images shown in FIG. 6 thereby respectively show the same slice as the image in FIG. 5. Shown on the left side is the image whose raw data were acquired during the first echo $E_1$ after an echo time $TE_1$=67 ms, and the right side shows an image whose raw data were acquired during the second echo $E_2$ after the second echo time $TE_2$=118 ms.

As FIG. 2 additionally shows, the diffusion-weighted image data $DID_1$, $DID_2$ can then be used within the scope of a parameter map combination MCO in order to achieve suitable parameter maps M with particular diagnostic significance. Moreover, the image data $RID_1$ that were reconstructed on the basis of the reference raw data $RRD_1$ that were acquired during the first echo are thereby used for an evaluation.

However, at this time these first reference image data $RID_1$ and the second reference image data $RID_2$ are used in order to generate a synthetic image at an effective echo time $TE_S$ between the first echo time and second echo time via an image combination WCO that is weighted per image point, as this was explained above using Equation (3). The effective echo time $TE_S$ depends on a weighting factor w that is freely selectable by the operator, for example.

Figure 7:
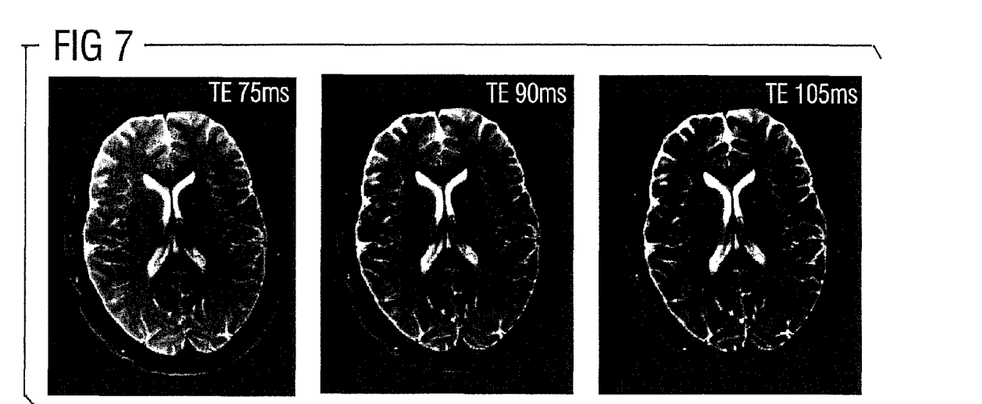
FIG. 7 shows three examples of synthetic $T_2$-weighted images generated at different effective echo times from the reference images according to FIG. 6.

In a reference measurement sequence RMS with partial reference sequences $RMS_i$ as they are shown in FIG. 4, both images that are determined from the raw data during the first echo $E_1$ and the second echo $E_2$ are spin echo data, meaning that $T_2$-weighted images are reconstructed from these. Three examples of such images are shown in FIG. 7, wherein the far left image shows a synthetic $T_2$-weighted image with an effective echo time $TE_S$=75 ms, the middle image shows a $T_2$-weighted image with an effective echo time $TE_S$=90 ms, and the right image shows a $T_2$-weighted image $IT_2$ with an echo time $TE_S$=105 ms. These $T_2$-weighted images do not differ from $T_2$-weighted images (under the assumption of a simple exponential $T_2$ decay) that were actually reconstructed on the basis of raw data that were really acquired within the scope of rs-EPI sequences with an echo time corresponding to the specified effective echo time $TE_S$.

Instead of the weighting factor w, the operator can also advantageously directly predetermine the desired effective echo time $TE_E$, which can then be converted automatically into a weighting factor w according to Equation (5) given a known first echo time $TE_1$ and known second echo time $TE_2$.

The invention thus allows the desired synthetic $T_2$-weighted image $IT_2$ to be provided to the operator immediately without an additional separate measurement being necessary to create $T_2$-weighted images.

Instead of $T_2$-weighted images, $T_2^*$-weighted images can also be generated in the manner according to the invention. These differ from $T_2$-weighted images only in that these are not spin echo data but rather gradient echo data.

Figure 8:
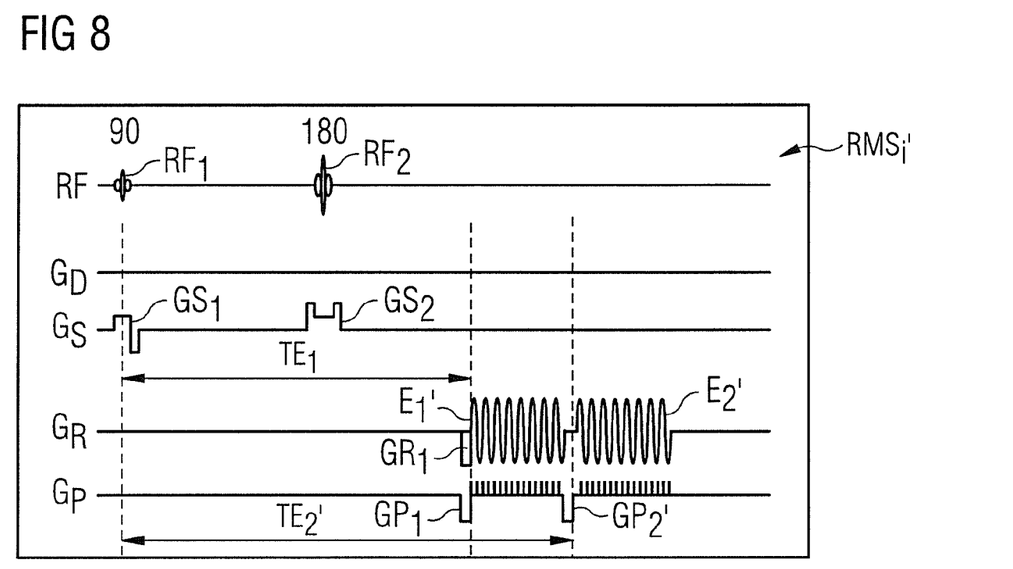
FIG. 8 is a pulse diagram of a partial reference sequence for an additional embodiment of the method according to the invention.

For this the reference measurement sequence RMS' must only be designed from somewhat modified partial reference sequences $RMS_i'$ as they are shown in FIG. 8. As is shown in comparison with the pulse diagram in FIG. 4, the partial reference sequences $RMS_i$ for a $T_2$-weighting differ from the partial reference sequences $RMS_i'$ for a $T_2^*$-weighting only in that now the second refocusing pulse $RF_3$ (and also accordingly the slice selection gradient pulse $GS_3$) is omitted in the partial reference sequence $RMS_i'$. Here the post-phase readout gradient pulse $GR_2$ and the second pre-phase readout gradient pulse $GR_3$ can then also be omitted accordingly, and the second and third phase coding gradient pulse $GP_2$, $GP_3$ are replaced by a single second phase coding gradient pulse $GP_2'$ in order to thus generate the second echo $E_2'$. In contrast to the first echo time $TE_1$ (which must be identical again to the first echo time $TE_1$ in the partial diffusion gradient sequences), this is not absolutely necessary for the second echo time $TE_2'$ since the second echo $E_2'$ is not used for a combination with the diffusion-coded data from the diffusion gradient measurement sequences; rather, only the raw data or, respectively, image data from the first echo $E_1$ are used.

The processing of the raw data acquired from this reference measurement sequence RMS' into corresponding reference image data and the combination of the reference image data $RED_1$, $RED_2$ into a $T_2^*$-weighted image $IT_2^*$ takes place analogously as in the generation of a $T_2$-weighted image $IT_2$ (as this is shown in FIG. 2). Equation (5) can also be used again for this. Although a $T_2$-weighting is also present in this sequence up to the first echo time $TE_1$, a $T_2^*$-weighting can be assumed between the first echo time $TE_1$ and the second echo time $TE_2'$ (and thus also between the first echo time $TE_1$ and the effective echo time $TE_E$). The same Equation (5) is therefore arrived at again with a procedure analogous to Equations (1) through (4).

Figure 9:
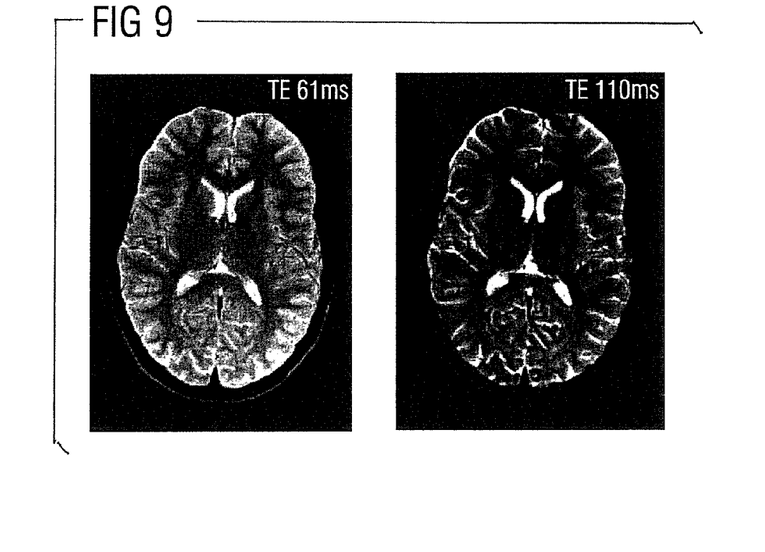
FIG. 9 shows examples of reference images of a slice through a human head, which reference images can be measured using partial reference sequences according to FIG. 8 at different echo times.

As an example, FIG. 9 shows two images that were generated on the basis of raw data that were acquired by means of partial reference sequences $RMS_i'$ as they were explained using the pulse diagram according to FIG. 8. The left image thereby shows an image generated from raw data that were measured during the first echo $E_1'$ after a first echo time $TE_1=61$ ms, and the right image is based on raw data that were acquired after the second echo time $TE_2$ 110 ms. In contrast to the images as they are shown in FIG. 6, these exposures were generated not only with a normal double echo rs-EPI sequence according to FIG. 8 but rather given a basic magnetic field of only 1.5 Tesla, an image matrix size of 214×214 pixels and a slice thickness of 5 mm. The field of view was again 220 mm.

Figure 10:
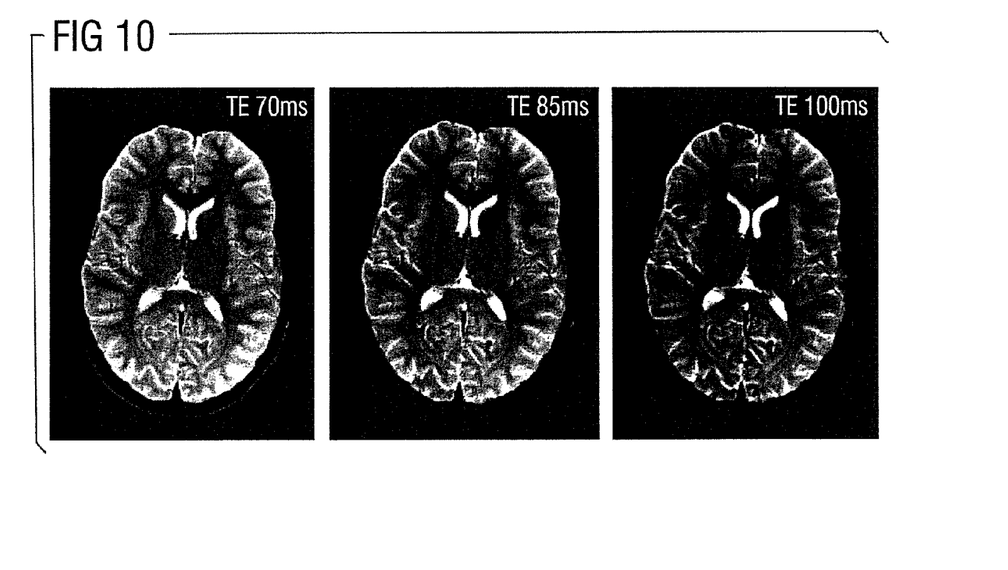
FIG. 10 shows three examples of synthetic $T_2^*$-weighted images generated at different effective echo times from the reference images according to FIG. 9.

FIG. 10 shows synthetic $T_2^*$-weighted images for different effective echo times $TE_S$ that were generated from these two images according to the method described in connection with Equation (3), namely the far left image for an effective echo time $TE_S=70$ ms, the middle image for an effective echo time of $TE_S=85$ ms and the right image for an effective echo time of $TE_S=100$ ms (these echo times again include a $T_2$-weighting up to the first echo time and following this a $T_2^*$-weighting). The images show that a generation of $T_2^*$-weighted images with the method according to the invention is also possible in a simple manner, which could be of interest in particular given a use of diffusion-weighted measurements for acute stroke patients since hemorrhages in the brain can be detected more quickly with such $T_2^*$-weighted images than with other images.

Although modifications and changes may be suggested by those skilled in the art, it is the intention of the inventor to embody within the patent warranted hereon all changes and modifications as reasonably and properly come within the scope of his contribution to the art.

In particular, as was already mentioned, the method for combination of the data from the various echoes into image data with a defined, effective echo time is not limited to the application in which reference data are used for diffusion-weighted measurements.

I claim as my invention:

1. A method to generate magnetic resonance exposures of an examination subject, comprising:
   operating a magnetic resonance data acquisition unit to acquire diffusion-coded raw data from an examination subject in the data acquisition unit, by executing a diffusion gradient measurement sequence comprising a plurality of successive partial diffusion gradient sequences;
   in each of said partial diffusion gradient sequences, emitting at least one diffusion coding gradient pulse, acquiring raw data during a first partial diffusion gradient sequence echo after a defined first partial diffusion gradient echo sequence time and entering said raw data into a k-space region of k-space, with the respective k-space regions acquired during respective different partial diffusion gradient sequences in total encompassing said k-space, and acquiring navigator raw data during a second partial diffusion gradient sequence echo after a defined second partial diffusion gradient sequence time and entering said navigator raw data into a predetermined navigator k-space region of k-space, said navigator k-space region being identical for each partial diffusion gradient sequence;
   acquiring reference raw data by operating said magnetic resonance data acquisition unit with a reference measurement sequence comprising a plurality of partial reference sequences; and
   in each of said partial reference sequences, acquiring first reference raw data during a first reference sequence echo after a first reference sequence echo time and entering said first reference raw data into a k-space region of k-space, the respective k-space regions into which said reference raw data are entered during respective different partial reference sequences in total encompassing all of said k-space, and acquiring second reference raw data during a second reference sequence echo at a second reference sequence echo time, and entering said second reference raw data into k-space regions, said k-space regions into which said second reference raw data are entered during respective different partial reference sequences in total encompassing all of said k-space.

2. A method as claimed in claim 1 comprising configuring said reference measurement sequence in order to allow image data to be reconstructed with a spatial resolution based on said first reference raw data and to allow image data with the same spatial resolution to be reconstructed based on the second reference raw data.

3. A method as claimed in claim 1 comprising operating said magnetic resonance data acquisition unit to emit a refocusing pulse in each of said partial reference sequences after said first partial reference sequence echo and before said second partial reference sequence echo.

4. A method as claimed in claim 1 comprising:
operating said magnetic resonance data acquisition unit to implement a plurality of diffusion gradient measurement sequences, each corresponding to said diffusion gradient measurement sequence, and executing each of said plurality of diffusion gradient measurement sequences with a respectively different diffusion gradient strength, in order to acquire a plurality of diffusion-coded raw data sets;
in a computer, reconstructing respective sets of image data, that are differently diffusion-weighted, from the respective sets of differently diffusion-coded raw data; and
in said computer, generating parameter maps as a combination of said image data sets.

5. A method as claimed in claim 1 comprising, in a computer, generating synthetic image data from said first reference raw data and said second reference raw data with a defined echo time outside of said first echo time and said second echo time.

6. A method as claimed in claim 5 wherein said defined echo time is between said first echo time and said second echo time.

7. A method to generate magnetic resonance exposures of an examination subject, comprising:
operating a magnetic resonance data acquisition unit to acquire diffusion-coded raw data from an examination subject in the data acquisition unit, by executing a diffusion gradient measurement sequence comprising a plurality of successive partial diffusion gradient sequences;
in each of said partial diffusion gradient sequences, emitting at least one diffusion coding gradient pulse, acquiring raw data during a first partial diffusion gradient sequence echo after a defined first partial diffusion gradient echo sequence time and entering said raw data into a k-space region of k-space, with the respective k-space regions acquired during respective different partial diffusion gradient sequences in total encompassing said k-space, and acquiring navigator raw data during a second partial diffusion gradient sequence echo after a defined second partial diffusion gradient sequence time and entering said navigator raw data into a predetermined navigator k-space region of k-space, said navigator k-space region being identical for each partial diffusion gradient sequence;
acquiring reference raw data by operating said magnetic resonance data acquisition unit with a reference measurement sequence comprising a plurality of partial reference sequences;
in each of said partial reference sequences, acquiring first reference raw data during a first reference sequence echo after a first reference sequence echo time and entering said first reference raw data into a k-space region of k-space, the respective k-space regions into which said reference raw data are entered during respective different partial reference sequences in total encompassing all of said k-space, and acquiring second reference raw data during a second reference sequence echo at a second reference sequence echo time, and entering said second reference raw data into k-space regions, said k-space regions into which said second reference raw data are entered during respective different partial reference sequences in total encompassing all of said k-space;
in a computer, generating first image data from said first raw data;
in said computer, generating second image data from said second raw data; and
generating synthetic image data with a defined echo time that is outside of said first echo time and said second echo, by geometrically averaging said first image data and said second image data.

8. A method as claimed in claim 7 wherein said defined echo time is between said first echo time and said second echo time.

9. A method as claimed in claim 7 comprising generating said synthetic image data by respectively weighting, with different predetermined weighting factors, said first image data and said second image data in said geometric averaging of said first image data and said second image data.

10. A magnetic resonance system comprising:
a magnetic resonance data acquisition unit;
a control unit configured to operate said magnetic resonance data acquisition unit to acquire diffusion-coded raw data from an examination subject in the data acquisition unit, by executing a diffusion gradient measurement sequence comprising a plurality of successive partial diffusion gradient sequences;
said control unit being configured to operate said magnetic resonance data acquisition unit to emit, in each of said partial diffusion gradient sequences, at least one diffusion coding gradient pulse, and to acquire raw data during a first partial diffusion gradient sequence echo after a defined first partial diffusion gradient echo sequence time and to enter said raw data into a k-space region of k-space, with the respective k-space regions acquired during respective different partial diffusion gradient sequences in total encompassing said k-space, and to acquire navigator raw data during a second partial diffusion gradient sequence echo after a defined second partial diffusion gradient sequence time and to enter said navigator raw data into a predetermined navigator k-space region of k-space, said navigator k-space region being identical for each partial diffusion gradient sequence;
said control unit being configured to operate said magnetic resonance data acquisition unit to acquire reference raw data with a reference measurement sequence comprising a plurality of partial reference sequences; and
said control unit being configured to operate said magnetic resonance data acquisition unit to, in each of said partial reference sequences, acquire first reference raw data during a first reference sequence echo after a first reference sequence echo time and to enter said first reference raw data into a k-space region of k-space, the respective k-space regions into which said reference raw data are entered during respective different partial reference sequences in total encompassing all of said k-space, and to acquire second reference raw data during a second reference sequence echo at a second reference sequence echo time, and to enter said second reference raw data into k-space regions, said k-space regions into which said second reference raw data are entered during respective different partial reference sequences in total encompassing all of said k-space.

11. A magnetic resonance system comprising:
a magnetic resonance data acquisition unit;
a control unit configured to operate said magnetic resonance data acquisition unit to acquire diffusion-coded raw data from an examination subject in the data acquisition unit, by executing a diffusion gradient measurement sequence comprising a plurality of successive partial diffusion gradient sequences;
said control unit being configured to operate said magnetic resonance data acquisition unit to emit, in each of said partial diffusion gradient sequences, at least one diffusion coding gradient pulse, and to acquire raw data during a first partial diffusion gradient sequence echo after a defined first partial diffusion gradient echo sequence time and to enter said raw data into a k-space region of k-space, with the respective k-space regions acquired during respective different partial diffusion gradient sequences in total encompassing said k-space, and to acquire navigator raw data during a second partial diffusion gradient sequence echo after a defined second partial diffusion gradient sequence time and to enter said navigator raw data into a predetermined navigator k-space region of k-space, said navigator k-space region being identical for each partial diffusion gradient sequence;

said control unit being configured to operate said magnetic resonance data acquisition unit to acquire reference raw data with a reference measurement sequence comprising a plurality of partial reference sequences;

said control unit being configured to operate said magnetic resonance data acquisition unit to, in each of said partial reference sequences, acquire first reference raw data during a first reference sequence echo after a first reference sequence echo time and to enter said first reference raw data into a k-space region of k-space, the respective k-space regions into which said reference raw data are entered during respective different partial reference sequences in total encompassing all of said k-space, and to acquire second reference raw data during a second reference sequence echo at a second reference sequence echo time, and to enter said second reference raw data into k-space regions, said k-space regions into which said second reference raw data are entered during respective different partial reference sequences in total encompassing all of said k-space;

a computer configured to generate first image data from said first raw data;

said computer being configured to generate second image data from said second raw data; and said computer being configured to generate synthetic image data with a defined echo time that is outside of said first echo time and said second echo, by geometrically averaging said first image data and said second image data.

12. A non-transitory, computer-readable data storage medium encoded with programming instructions, said data storage medium being loaded into a computerized control and evaluation unit of a magnetic resonance system, said magnetic resonance system comprising a magnetic resonance data acquisition unit, and said programming instructions causing said computerized control and evaluation system to:

operate said magnetic resonance data acquisition unit to acquire diffusion-coded raw data from an examination subject in the data acquisition unit, by executing a diffusion gradient measurement sequence comprising a plurality of successive partial diffusion gradient sequences;

operate said magnetic resonance data acquisition unit to emit, in each of said partial diffusion gradient sequences, at least one diffusion coding gradient pulse, in order to acquire raw data during a first partial diffusion gradient sequence echo after a defined first partial diffusion gradient echo sequence time and enter said raw data into a k-space region of k-space, with the respective k-space regions acquired during respective different partial diffusion gradient sequences in total encompassing said k-space, and in order to acquire navigator raw data during a second partial diffusion gradient sequence echo after a defined second partial diffusion gradient sequence time and enter said navigator raw data into a predetermined navigator k-space region of k-space, said navigator k-space region being identical for each partial diffusion gradient sequence;

acquire reference raw data by operating said magnetic resonance data acquisition unit with a reference measurement sequence comprising a plurality of partial reference sequences; and operate said magnetic resonance data acquisition unit to acquire, in each of said partial reference sequences, first reference raw data during a first reference sequence echo after a first reference sequence echo time and enter said first reference raw data into a k-space region of k-space, the respective k-space regions into which said reference raw data are entered during respective different partial reference sequences in total encompassing all of said k-space, and to acquire second reference raw data during a second reference sequence echo at a second reference sequence echo time, and enter said second reference raw data into k-space regions, said k-space regions into which said second reference raw data are entered during respective different partial reference sequences in total encompassing all of said k-space.

13. A non-transitory, computer-readable data storage medium encoded with programming instructions, said data storage medium being loaded into a computerized control and evaluation unit of a magnetic resonance system, said magnetic resonance system comprising a magnetic resonance data acquisition unit, and said programming instructions causing said computerized control and evaluation system to:

operate a magnetic resonance data acquisition unit to acquire diffusion-coded raw data from an examination subject in the data acquisition unit, by executing a diffusion gradient measurement sequence comprising a plurality of successive partial diffusion gradient sequences;

operate said magnetic resonance data acquisition unit to emit, in each of said partial diffusion gradient sequences, at least one diffusion coding gradient pulse, in order to acquire raw data during a first partial diffusion gradient sequence echo after a defined first partial diffusion gradient echo sequence time and enter said raw data into a k-space region of k-space, with the respective k-space regions acquired during respective different partial diffusion gradient sequences in total encompassing said k-space, and in order to acquire navigator raw data during a second partial diffusion gradient sequence echo after a defined second partial diffusion gradient sequence time and enter said navigator raw data into a predetermined navigator k-space region of k-space, said navigator k-space region being identical for each partial diffusion gradient sequence;

acquire reference raw data by operating said magnetic resonance data acquisition unit with a reference measurement sequence comprising a plurality of partial reference sequences;

operate said magnetic resonance data acquisition unit to acquire, in each of said partial reference sequences, first reference raw data during a first reference sequence echo after a first reference sequence echo time and enter said first reference raw data into a k-space region of k-space, the respective k-space regions into which said reference raw data are entered during respective different partial reference sequences in total encompassing all of said k-space, and to acquire second reference raw data during a second reference sequence echo at a second reference sequence echo time, and enter said second reference raw data into k-space regions, said k-space regions into which said second reference raw data are entered during respective different partial reference sequences in total encompassing all of said k-space;

generate first image data from said first raw data;

generate second image data from said second raw data; and generate synthetic image data with a defined echo time that is outside of said first echo time and said second echo, by geometrically averaging said first image data and said second image data.

* * * * *